United States Patent
Weinberg et al.

(10) Patent No.: US 9,612,308 B2
(45) Date of Patent: Apr. 4, 2017

(54) ULTRA-FAST MAGNETIC FIELD FOR ELECTRON PARAMAGNETIC RESONANCE IMAGING USED IN MONITORING DOSE FROM PROTON OR HADRON THERAPY

(75) Inventors: Irving N. Weinberg, Bethesda, MD (US); Stanley Thomas Fricke, Bethesda, MD (US)

(73) Assignee: WEINBERG MEDICAL PHYSICS INC, North Bethesda, MD (US)

( * ) Notice: Subject to any disclaimer, the term of this patent is extended or adjusted under 35 U.S.C. 154(b) by 1107 days.

(21) Appl. No.: 13/475,005

(22) Filed: May 18, 2012

(65) Prior Publication Data

US 2012/0326722 A1 Dec. 27, 2012

Related U.S. Application Data

(63) Continuation-in-part of application No. 13/439,382, filed on Apr. 4, 2012, now Pat. No. 9,411,030, and a continuation-in-part of application No. 12/888,580, filed on Sep. 23, 2010, now Pat. No. 8,836,329, and a continuation-in-part of application No. 12/905,256, filed on Oct. 15, 2010, now Pat. No. 8,466,680, and a continuation-in-part of application No. 12/488,105, filed on Jun. 19, 2009, now Pat. No. 8,154,286.

(60) Provisional application No. 61/488,819, filed on May 23, 2011, provisional application No. 61/074,397, filed on Jun. 20, 2008.

(51) Int. Cl.
| | | |
|---|---|---|
| G01V 3/00 | (2006.01) | |
| G01R 33/60 | (2006.01) | |
| G01R 33/48 | (2006.01) | |
| A61N 5/10 | (2006.01) | |

(52) U.S. Cl.
CPC ........... *G01R 33/60* (2013.01); *A61N 5/1071* (2013.01); *A61N 2005/1055* (2013.01); *A61N 2005/1087* (2013.01); *G01R 33/4808* (2013.01)

(58) Field of Classification Search
CPC ...................................................... G01R 33/60
USPC .................................................. 324/316, 300
See application file for complete search history.

(56) References Cited

U.S. PATENT DOCUMENTS

| | | |
|---|---|---|
| 5,415,163 A | 5/1995 | Harms et al. |
| 5,442,290 A | 8/1995 | Crooks |
| | (Continued) | |

FOREIGN PATENT DOCUMENTS

| | | |
|---|---|---|
| EP | 2294436 A1 | 3/2011 |
| JP | 246827 | 2/1990 |
| WO | 2009155522 A1 | 12/2009 |

OTHER PUBLICATIONS

Junk, J. N.; Electron Paramagnetic Resonance Theory; Assessing the Functional Structure of Molecular Transporters by EPR Spectroscopy; 2012; p. 11; Springer; ISBN 978-3-642-25134-4.
(Continued)

*Primary Examiner* — Louis Arana
(74) *Attorney, Agent, or Firm* — Barnes & Thornburg LLP

(57) ABSTRACT

Instrumentation and methodologies are provided that enable the direct measurement of free radicals generated in patients as a result of radiation therapy through the use of proton beams and other forms of ionizing radiation. As a result, in accordance with at least one disclosed embodiment, the instrumentation and methodologies may be used in conjunction with radiation therapy to detect, monitor and/or control generation of free radicals in cancerous tissue during such radiation therapy.

23 Claims, 1 Drawing Sheet

(56) References Cited

U.S. PATENT DOCUMENTS

| | | | |
|---|---|---|---|
| 6,133,733 A * | 10/2000 | Lurie et al. | 324/300 |
| 6,150,821 A | 11/2000 | Mori et al. | |
| 6,198,282 B1 * | 3/2001 | Dumoulin | 324/307 |
| 6,704,594 B1 | 3/2004 | Blank et al. | |
| 7,047,062 B2 * | 5/2006 | Licato et al. | 600/410 |
| 7,859,260 B2 | 12/2010 | Reiderman | |
| 8,154,286 B2 | 4/2012 | Weinberg | |
| 8,466,680 B2 | 6/2013 | Weinberg et al. | |
| 8,836,329 B2 | 9/2014 | Weinberg | |
| 2009/0149735 A1 | 6/2009 | Fallone et al. | |
| 2009/0251141 A1 | 10/2009 | Baumgartl et al. | |
| 2009/0315560 A1 | 12/2009 | Weinberg | |
| 2010/0295641 A1 | 11/2010 | Schild et al. | |
| 2011/0068791 A1 | 3/2011 | Weinberg | |
| 2011/0089947 A1 | 4/2011 | Weinberg et al. | |
| 2012/0223711 A1 | 9/2012 | Weinberg | |
| 2014/0097842 A1 * | 4/2014 | Yang et al. | 324/316 |

OTHER PUBLICATIONS

Bauer et al., "Innovative Efficient Gradient Coil Driver Toplogy," IEEE, (2004), pp. 1838-1843.

Bertora et al., "Transversal Gradient Compensation in Three-Sided MRI Magnets," Robotics, Brain and Cognitive Sciences, Italian Institute of Technology, (2009) p. 3056.

Conradi, "Generation of Short, Intense Gradient Pulses", Journal of Magnetic Resonance vol. 94, No. 2, (1991), pp. 370-375.

Glover, "Interaction of MRI Field Gradients With the Human Body", Phys. Med. Biol. vol. 54, (2009), pp. R99-R115.

Harvey et al., "Avoiding Peripheral Nerve Stimulation: Gradient Waveform Criteria for Optimum Resolution in Echo-Planar Imaging", MRM, (1994), pp. 236-241.

ICNIRP Guidelines, "For Limiting Exposure to Time-Varying Electric, Magnetic and Electromagnetic Fields," Health Physics 74(4), pp. 493-523 (1998).

International Standard, "Particular Requirements for the Basic Safety and Essential Performance of Magnetic Resonance Equipment for Medical Diagnosis", (2010), p. 1-224.

Joachim et al., "Peripheral Nerve Stimulation by Time-Varying Magnetic Fields", Journal of Computer Assisted Tomography, vol. 21(4), (1997), pp. 532-538.

Mueller et al., "A High-Efficiency 4-Switch GOT Speed-Up Inverter for the Generation of Fast-Changing MRI Gradient Fields", pp. 806-812 (1993).

Reichert et al., "Magnetic Resonance Imaging of Cortical Bone With Ultrashort TE Pulse Sequences", Magnetic Resonance Imaging, 23, (2005), pp. 611-618.

Reilly, "Maximum Pulsed Electromagnetic Field Limits Based on Peripheral Nerve Stimulation: Application to IEEE/ANSI C95.1 Electromagnetic Field Standards," IEEE Transactions on Biomedical Engineering, vol. 45, No. 1, (1998), pp. 137-141.

Riepe, "High-Voltage Microsecond Pulse-Forming Network", pp. 1028-1030 (1977).

Sanders et al., "High Power Solid State Switch Module", IEEE, (2004), pp. 563-566.

Vogt et al., "Increased Time Rate of Change of Gradient Fields: Effect on Peripheral Nerve Stimulation at Clinical MR Imaging", Radiology, (2004), pp. 548-554.

Zupanete et al., "Coils Producing a Magnetic Field Gradient for Diffusion Measurements With NMR", pp. 79-80 (1975).

* cited by examiner

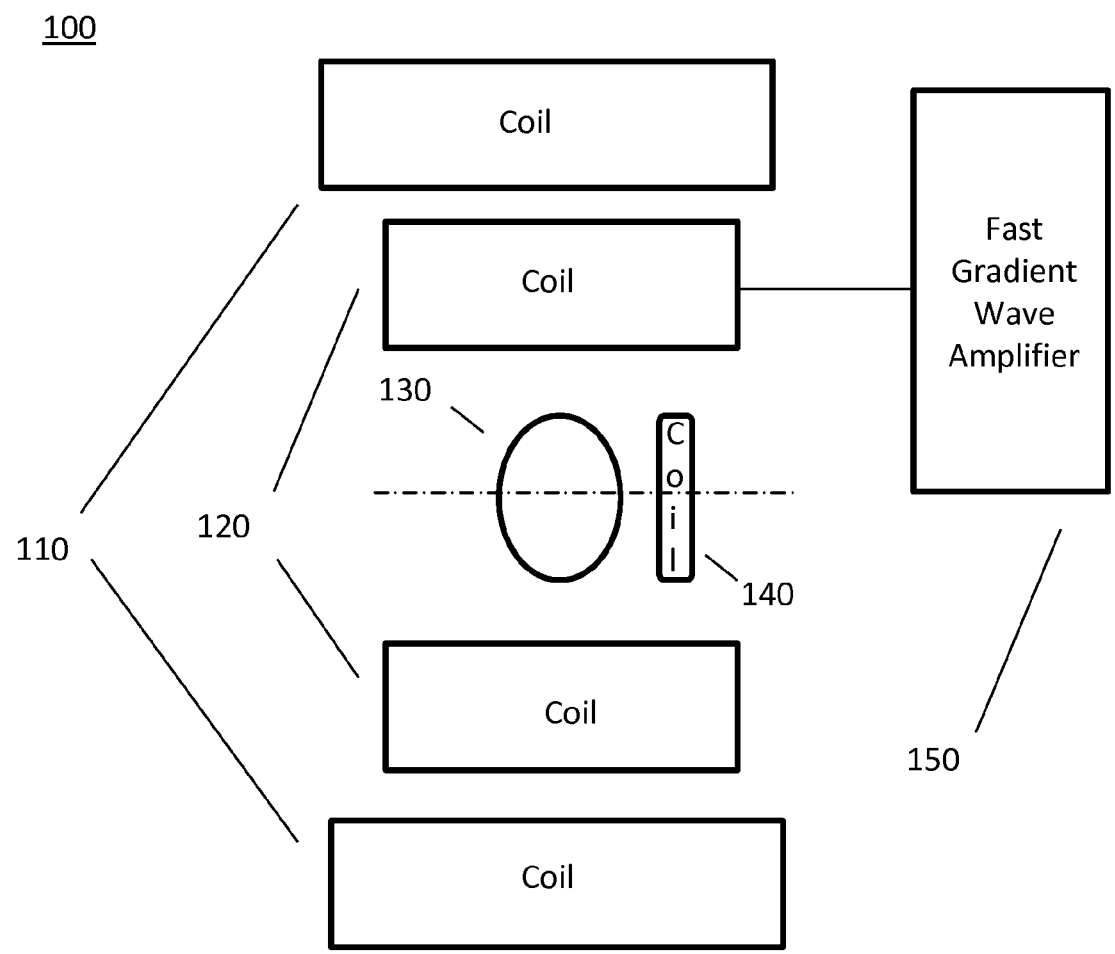

ULTRA-FAST MAGNETIC FIELD FOR ELECTRON PARAMAGNETIC RESONANCE IMAGING USED IN MONITORING DOSE FROM PROTON OR HADRON THERAPY

CROSS-REFERENCE TO RELATED APPLICATION(S)

This application relies for priority on U.S. Provisional Patent Application Ser. No. 61/488,819, filed on May 23, 2011, the entirety of which being incorporated by reference herein. The present application also claims the benefit, under 35 U.S.C. 120, of U.S. patent application Ser. Nos. 13/439, 382, 12/888,580, 12/905,256, as a continuation-in-part application, each of those patent applications claiming the benefit of and incorporating by reference U.S. patent application Ser. No. 12/488,105, entitled "APPARATUS AND METHOD FOR DECREASING BIO-EFFECTS OF MAGNETIC FIELDS, which has issued as U.S. Pat. No. 8,154,286.

FIELD OF THE INVENTION

Disclosed embodiments are directed, generally, to electron paramagnetic resonance imaging used in monitoring dose.

DESCRIPTION OF THE RELATED ART

External beam, radiation therapy can often be improved by estimating the radiation dose received by the patient based on monitoring. This monitoring is traditionally accomplished by placement of a "phantom" in the expected location of the part of the patient irradiated. A phantom is a physical model of a portion of the patient, generally containing materials having physical properties that are as close as possible to that of the patient's. The phantom is generally equipped with an instrument (e.g., a dosimeter) that can keep track of the amount of radiation exposure to one or more locations within the phantom.

Proton therapy is a form of radiation therapy in which energetic protons are aimed at structures of interest (for example, cancer foci) within a patient. Beams of other particles such as neutrons or carbon atoms may also be aimed at a patient, and this practice is generally known as hadron therapy.

It is known that hadron therapy may be monitored based on the collection of gamma rays that are generated within the patient, which are a direct or indirect result of nuclear reactions in the atoms within the patient. For example, a Positron Emission Tomography (PET) scanner may be used to form an image using the gamma rays generated by the decay of carbon-11 (i.e., a positron emitter), which is formed from carbon-12, nitrogen-14 and/or oxygen-16 in the patient as a result of proton or hadron beam therapy. Alternatively, a different type of imaging instrument (e.g., a gamma camera) can be used to form images using gamma rays emitted by activated elements within the patient (so-called "prompt coincidences").

It is known that proton beams and other forms of ionizing radiation can create free-radicals, which are usually defined as uncharged molecules containing an unpaired valence electron. The generation of free radicals in cancerous tissue is one of the key aims of radiation therapy, since these free radicals are involved in destroying the genetic material of the cancer cells. However, there are no existing instruments for directly assessing the presence of free radicals in patients after radiation therapy.

It is known that proton beams and other forms of ionizing radiation can create free-radicals, which are usually defined as uncharged molecules containing an unpaired valence electron. The generation of free radicals in cancerous tissue is one of the key aims of radiation therapy, since these free radicals are involved in destroying the genetic material of the cancer cells. However, there are no existing instruments for directly assessing the presence of free radicals in patients after radiation therapy.

SUMMARY

The following presents a simplified summary in order to provide a basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to the more detailed description below.

In accordance with at least one disclosed embodiment, instrumentation and methodologies are provided that enable the direct measurement of free radicals generated in patients as a result of radiation therapy through the use of proton beams and other forms of ionizing radiation. As a result, in accordance with at least one disclosed embodiment, the instrumentation and methodologies may be used in conjunction with radiation therapy to detect, monitor and/or control generation of free radicals in cancerous tissue during such radiation therapy.

BRIEF DESCRIPTION OF THE DRAWINGS

A more compete understanding of the present invention and the utility thereof may be acquired by referring to the following description in consideration of the accompanying drawings, in which like reference numbers indicate like features, and wherein:

FIG. 1 illustrates one example of an apparatus 100 provided in accordance with the disclosed embodiments.

DETAILED DESCRIPTION

The description of specific embodiments is not intended to be limiting of the present invention. To the contrary, those skilled in the art should appreciate that there are numerous variations and equivalents that may be employed without departing from the scope of the present invention. Those equivalents and variations are intended to be encompassed by the present invention.

In the following description of various invention embodiments, reference is made to the accompanying drawings, which form a part hereof, and in which is shown, by way of illustration, various embodiments in which the invention may be practiced. It is to be understood that other embodiments may be utilized and structural and functional modifications may be made without departing from the scope and spirit of the present invention.

As explained above, in accordance with at least one disclosed embodiment, instrumentation and methodologies are provided that enable the direct measurement of free radicals generated in patients as a result of radiation therapy through the use of proton beams and other forms of ionizing radiation. As a result, in accordance with at least one disclosed embodiment, the instrumentation and methodologies may be used in conjunction with radiation therapy to detect, monitor and/or control generation of free radicals in cancerous tissue during such radiation therapy.

Free radicals occur in scenarios other than radiation therapy. Foods can spoil due to the generation of free radicals by sunlight, which is one reason that many foods are packed in nitrogen. In the laboratory, free radical concentration can be measured with a technique known as Electron Spin Resonance (ESR), also known as Electron Paramagnetic Resonance (EPR).

EPR takes advantage of the presence of unpaired valence electrons (or other forms of free electrons), by splitting the energy states of the electron as a result of application of a magnetic field. Accordingly, the free electron can be moved from a lower energy state to an upper energy state as a result of application of a Radio Frequency (RF) pulse of appropriate frequency (i.e., the resonance frequency). The measurement of energy loss in this transformation is often termed "ESR spectroscopy."

Conventional methods and mechanisms exist for the magnetization of an ensemble of electrons as a group, whose behavior follows the Bloch equations, as shown in many publications, for example the book "Assessing the Functional Structure of Molecular Transporters by EPR Spectroscopy, by J. N. Junk, published by Springer in 2012, ISBN 978-3-642-25134-4, on page 11.

The summed magnetic vectors of each electron can be considered as a single magnetization vector; thus, if the electrons are immersed in a magnetic field, the magnetization vector of the electron ensemble rotates around an axis (i.e., precesses) like a spinning top that has been pushed from the vertical position. This electron precession is similar to the phenomenon employed to produce magnetic resonance imaging of protons, which results from the precession of protons in water atoms of the human body.

In proton Magnetic Resonance Imaging (which is denoted herein, simply, as MRI), the judicious application of RF pulses to initiate precession, and of the application of magnetic gradients to a sample, spatially label the sample in precessional frequencies and phases as a function of spatial location. After encoding the sample a radio frequency receiver is turned on to receive the sample's transmission of its encoded frequencies and phases. Next a Fourier transform is preformed on this received signal and an MRI image is create of the proton distribution in the body.

Theoretically, pulse sequences devised for proton MRI can be applied to electrons as well. Because of the much smaller mass of the electron as compared to the proton, the RF frequency for this type of imaging (denoted as electron paramagnetic resonance imaging, or "EPRI") at a given imposed magnetic field is almost 2,000 times higher than for proton MRI. Additionally, the decay time of the pulse emitted by the electron ensemble is typically much shorter than in MRI. Thus, a typical relaxation time for a spin-echo generated by an unbound free-radical in EPRI is several microseconds. However, typical pulse generators and magnetic coils employed in MRI systems have pulses that are much longer than this short time period. However, in accordance with at least one disclosed embodiment, methodologies and mechanisms are provided that more effectively handle this timing requirement.

EPRI has been used conventionally in conjunction with the application of intravenously-administered spin-traps, which are materials that grab free radicals and lengthen the lifetime of the free radicals. One such application was described by K. Matsumoto, S. Subramanian, R. Murugesan, J. B. Mitchell, and M. C. Krishna, in the journal "Antioxidant Redox Signal", published in 2007 (volume 9, pages 1125-41), entitled "Spatially resolved biological information from in vivo EPRI, OMRI, and MRI" (incorporated herein by reference in its entirety). However, the use of injectable spin traps to measure free radicals is not advantageous, useful or effective in radiation therapy because the efficacy of radiation therapy depends on the presence of unbound free radicals.

It is known that free-radicals caused by application of a proton beam to certain biological materials without spin traps can last for weeks or longer (see, F Trompier, C Bassinet, A Wieser, C De Angelis, D Viscomi, P Fattibene, entitled "Radiation-induced signals analysed by EPR spectrometry applied to fortuitous dosimetry", published in the Journal Ann 1st Super Sanita, volume 43, number 3, page 287-296, 2009, incorporated herein by reference in its entirety). Although Trompier et al. analyzed hair, plastic, and sugar after exposure to radiation, hydrated tissues have free-radical lifetimes that are in the microsecond range.

In accordance with at least one disclosed embodiment, methodologies and mechanisms are provided that more effectively address the monitoring of dose within hydrated tissues.

In accordance with at least one disclosed embodiment, a rapidly changing magnetic field is applied in pulse sequences for realizing EPRI of a body part that has been exposed to ionizing radiation. The rapidly changing magnetic field may have a rise-time and fall-time of less than 10 microseconds, as in our prior patent application. As disclosed in that patent application, it has been determined that a short ramp time results in reduced bio-effects (e.g., peripheral nerve stimulation) than is produced by conventionally used, longer ramp durations.

The magnetic field applied in accordance with the presently disclosed methodologies and mechanisms may be spatially inhomogeneous, that is, it causes a magnetic gradient in space to be realized.

In accordance with at least one disclosed embodiment, an apparatus comprises a pulse generator configured and operated to create magnetic and/or electromagnetic pulses and/or gradients with short enough times to yield EPRI images of biological tissues. The tissues may be imaged during or after application of radiation or other therapy, in order to measure the presence of free-radicals induced by these therapeutic modalities.

Likewise, in accordance with at least one disclosed embodiment, application of the inventive concept to measurements after the use of a hadron beam enables an effective mechanism and methodology for obtaining valuable information regarding free-radicals generated by the therapy.

Thus, it should be understood that the inventive methodologies and mechanisms encompass the apparatus configuration for monitoring the free radicals but also a methodology for using pulse sequences with very short rise-times, fall-times, and/or durations, which are required for collecting data from free-radicals that may have short lifetimes, e.g., biological tissues.

FIG. 1 illustrates one example of an apparatus 100 provided in accordance with the disclosed embodiments. As shown in FIG. 1, coils 110 impose a static field and coils 120 impose time varying gradient magnetic fields on biological tissue 130.

RF energy is transmitted and received by coil assembly 140.

In quantitative measurements, the area under the peak of the Fourier transform of the received time domain signal is directly proportional to the number of free radicals liberated. In subjective measurements the intensity of a pixel in an image of the same is also directly proportional to the number of free radicals liberated. The reason for this is that the induced electromotive force into the "pick-up" or receiving radio-frequency antenna is multiplied by the actual number of electrons "spinning" or changing state.

Fast gradient waveform amplifier 150 supplies power to one or more of coils 110, 120 and/or 140. It should be understood that any or all of coils 110, 120 and/or 140 may be combined into a single coil assembly. It should also be appreciated that the static field imposed by coil 110 may be replaced by a "quasi-static" magnetic field which is constant over the time course of the measurement of the electronic precession, or by a source whose magnetic field may vary over the time course of the measurement.

Disclosed mechanisms and methodologies may be used repeatedly for the monitoring of a patient's body, in the case that the body receives multiple doses of radiation and it is desired to determine the exposure from one or more specific doses.

Examination of the body may be conducted rapidly due to the short pulse duration, so that the entire examination may be concluded in seconds or less, thereby facilitating the monitoring process. Changes in the treatment plan for the body may be contemplated by a user as a result of the data generated by the methodologies and mechanism provided in accordance with the disclosed embodiments.

It should be understood that various connections are set forth between elements in the following description; however, these connections in general, and, unless otherwise specified, may be either direct or indirect, either permanent or transitory, and either dedicated or shared, and that this specification is not intended to be limiting in this respect.

While this invention has been described in conjunction with the specific embodiments outlined above, it is evident that many alternatives, modifications and variations will be apparent to those skilled in the art. Accordingly, the various embodiments of the invention, as set forth above, are intended to be illustrative, not limiting. Various changes may be made without departing from the spirit and scope of the invention.

Additionally, it should be understood that the functionality described in connection with various described components of various invention embodiments may be combined or separated from one another in such a way that the architecture of the invention is somewhat different than what is expressly disclosed herein. Moreover, it should be understood that, unless otherwise specified, there is no essential requirement that methodology operations be performed in the illustrated order; therefore, one of ordinary skill in the art would recognize that some operations may be performed in one or more alternative order and/or simultaneously.

Various components of the invention may be provided in alternative combinations operated by, under the control of or on the behalf of various different entities or individuals.

Further, it should be understood that, in accordance with at least one embodiment of the invention, system components may be implemented together or separately and there may be one or more of any or all of the disclosed system components. Further, system components may be either dedicated systems or such functionality may be implemented as virtual systems implemented on general purpose equipment via software implementations.

As a result, it will be apparent for those skilled in the art that the illustrative embodiments described are only examples and that various modifications can be made within the scope of the invention as defined in the appended claims.

What is claimed is:

1. A method for applying electron paramagnetic resonance imaging to living biological tissue exposed to ionizing radiation, the method comprising:
   imposing a magnetic field on the living biological tissue while imposing gradient pulses on the biological tissue; and
   obtaining data indicating an amount of free radicals in the living biological tissue generated as a result of the exposure to ionizing radiation,
   wherein one or more magnetic fields are applied in at least one pulse, and with a ramp of the at least one pulse lasting less than 10 microseconds.

2. The method of claim 1, wherein the imposed magnetic field is a static magnetic field.

3. The method of claim 1, wherein the imposed magnetic field is a quasi-static magnetic field.

4. The method of claim 1, wherein the imposed magnetic field is a dynamic magnetic field.

5. The method of claim 1, further comprising monitoring distribution of dose or exposure in the living biological tissue.

6. The method of claim 1, further comprising monitoring an effect of exposure to ionizing radiation in the living biological tissue.

7. The method of claim 1, wherein the one or magnetic fields are rapidly changing and applied in pulse sequences for electron paramagnetic resonance imaging, and wherein the rapidly changing magnetic fields have rise-times and fall-times of less than 10 microseconds.

8. The method of claim 1, with a duration of the at least one pulse being less than 10 microseconds.

9. The method of claim 1, wherein the ionizing radiation is proton therapy.

10. The method of claim 1, wherein the ionizing radiation is hadron therapy.

11. The method of claim 1, wherein a sub-second duration of the entire pulse sequence is required to form an image.

12. The method of claim 1, further comprising using the data obtained from monitoring dose to adjust a next administered ionizing radiation dose.

13. A method for applying electron paramagnetic resonance imaging to living biological tissue exposed to ionizing radiation, the method comprising:
   imposing a magnetic field on the living biological tissue while imposing gradient pulses on the biological tissue; and
   monitoring distribution of dose or exposure of the ionizing radiation in the living biological tissue,
   wherein one or more magnetic fields are applied in at least one pulse, and with a ramp of the at least one pulse lasting less than 10 microseconds.

14. The method of claim 13, wherein the imposed magnetic field is a static magnetic field.

15. The method of claim 13, wherein the imposed magnetic field is a quasi-static magnetic field.

16. The method of claim 13, wherein the imposed magnetic field is a dynamic magnetic field.

17. The method of claim 13, further comprising monitoring an effect of exposure to ionizing radiation in the living biological tissue.

18. The method of claim 13, wherein the one or magnetic fields are rapidly changing and applied in pulse sequences for electron paramagnetic resonance imaging, and wherein the rapidly changing magnetic fields have rise-times and fall-times of less than 10 microseconds.

19. The method of claim 13, with a duration of the at least one pulse being less than 10 microseconds.

20. The method of claim 13, wherein the ionizing radiation is proton therapy.

21. The method of claim 13, wherein the ionizing radiation is hadron therapy.

22. The method of claim 13, wherein a sub-second duration of the entire pulse sequence is required to form an image.

23. The method of claim 13, further comprising using the data obtained from monitoring dose to adjust a next administered ionizing radiation dose.

* * * * *